(12) United States Patent
Xiao

(10) Patent No.: US 11,383,071 B2
(45) Date of Patent: Jul. 12, 2022

(54) TATTOO DEVICE WITH MOTOR HAVING BUILT-IN MOTION CONVERSION MEMBER

(71) Applicant: Long Xiao, Scarborough (CA)

(72) Inventor: Long Xiao, Scarborough (CA)

( * ) Notice: Subject to any disclaimer, the term of this patent is extended or adjusted under 35 U.S.C. 154(b) by 366 days.

(21) Appl. No.: 16/814,738

(22) Filed: Mar. 10, 2020

(65) Prior Publication Data
US 2021/0283389 A1     Sep. 16, 2021

(51) Int. Cl.
| *A61M 37/00* | (2006.01) |
| *H02K 7/06* | (2006.01) |
| *H02K 7/08* | (2006.01) |
| *H02K 7/075* | (2006.01) |

(52) U.S. Cl.
CPC .......... *A61M 37/0076* (2013.01); *H02K 7/06* (2013.01); *H02K 7/061* (2013.01); *H02K 7/08* (2013.01); *H02K 7/075* (2013.01)

(58) Field of Classification Search
CPC ..... A61M 37/0076; H02K 7/06; H02K 7/061; H02K 7/08; H02K 7/075
See application file for complete search history.

(56) References Cited

U.S. PATENT DOCUMENTS

| 3,274,795 | A | * | 9/1966 | Fowle | F25B 9/06 |
| | | | | | 417/500 |
| 3,327,826 | A | * | 6/1967 | Henschke | F16K 31/047 |
| | | | | | 74/89.34 |
| 5,551,319 | A | | 9/1996 | Spaulding et al. | |
| 6,325,157 | B1 | * | 12/2001 | Arakawa | B25D 16/00 |
| | | | | | 173/171 |
| 7,135,691 | B2 | * | 11/2006 | Vanderpot | H01L 21/68792 |
| | | | | | 250/492.1 |
| 7,137,489 | B2 | * | 11/2006 | Bastholm | F16H 25/2454 |
| | | | | | 188/162 |
| 7,207,242 | B1 | | 4/2007 | Daigle | |
| 7,308,950 | B2 | * | 12/2007 | Faatz | B25F 5/008 |
| | | | | | 173/171 |
| 7,755,315 | B2 | * | 7/2010 | Bott | H02K 16/00 |
| | | | | | 318/538 |
| 8,026,640 | B2 | * | 9/2011 | Bott | H02K 9/20 |
| | | | | | 310/15 |
| 9,126,320 | B2 | * | 9/2015 | Shinma | B25F 5/008 |
| 9,347,439 | B2 | * | 5/2016 | McColl | F04B 49/12 |

(Continued)

FOREIGN PATENT DOCUMENTS

| DE | 10306459 A1 | 11/2004 |
| WO | WO2014/065726 A1 | 5/2014 |

OTHER PUBLICATIONS

Extended European Search Report dated Aug. 18, 2021 issued in European Patent Application No. 21160945.8 (10 pages).

*Primary Examiner* — Pedro J Cuevas

(57) ABSTRACT

A tattoo device includes a rotary motor having a built-in motion conversion coupling. The device comprises a frame and an actuator for actuating a needle-driving shaft. The actuator includes an electric motor comprising a stator mounted to the frame, first and second bearings mounted to the frame, and a rotor comprising a rotor shaft rotatably supported at the first and second bearings, and a motion conversion member for converting rotation motion of the rotor to translation motion for reciprocally actuating the needle-driving shaft. The motion conversion member is positioned between the first and second bearings.

23 Claims, 16 Drawing Sheets

(56) References Cited

U.S. PATENT DOCUMENTS

| | | |
|---|---|---|
| 9,393,395 B2 | 7/2016 | Miller et al. |
| 9,662,483 B2 | 5/2017 | Siciliano |
| 9,827,409 B1 | 11/2017 | Evans et al. |
| 10,830,320 B2 * | 11/2020 | Matsuto ................. F16H 57/021 |
| 11,052,530 B2 * | 7/2021 | Matsushita ............... H02P 6/16 |
| 11,101,716 B2 * | 8/2021 | Matsuto ................... H02K 7/06 |
| 2005/0230643 A1 * | 10/2005 | Vanderpot ......... H01L 21/67069 |
| | | 250/492.21 |
| 2009/0039713 A1 * | 2/2009 | Bott ........................ H02K 9/20 |
| | | 310/12.09 |
| 2013/0123825 A1 | 5/2013 | Demjanenko |
| 2015/0219081 A1 * | 8/2015 | McColl ................... F04B 49/12 |
| | | 417/415 |
| 2015/0352346 A1 | 12/2015 | Webb |
| 2017/0239804 A1 * | 8/2017 | Matsushita ............ H02K 11/33 |
| 2018/0369553 A1 | 12/2018 | Siciliano |
| 2019/0040939 A1 * | 2/2019 | Matsuto .............. F16H 25/2015 |
| 2019/0044409 A1 * | 2/2019 | Matsuto .............. H02K 5/1735 |
| 2019/0060626 A1 | 2/2019 | Xiao |
| 2019/0072163 A1 * | 3/2019 | Matsuto ................. F16H 25/20 |
| 2019/0085957 A1 * | 3/2019 | Matsuto ............. F16H 25/2204 |
| 2019/0217072 A1 | 7/2019 | Xiao |
| 2022/0134524 A1 * | 5/2022 | Shioya ................... B25C 1/047 |
| | | 227/130 |

* cited by examiner

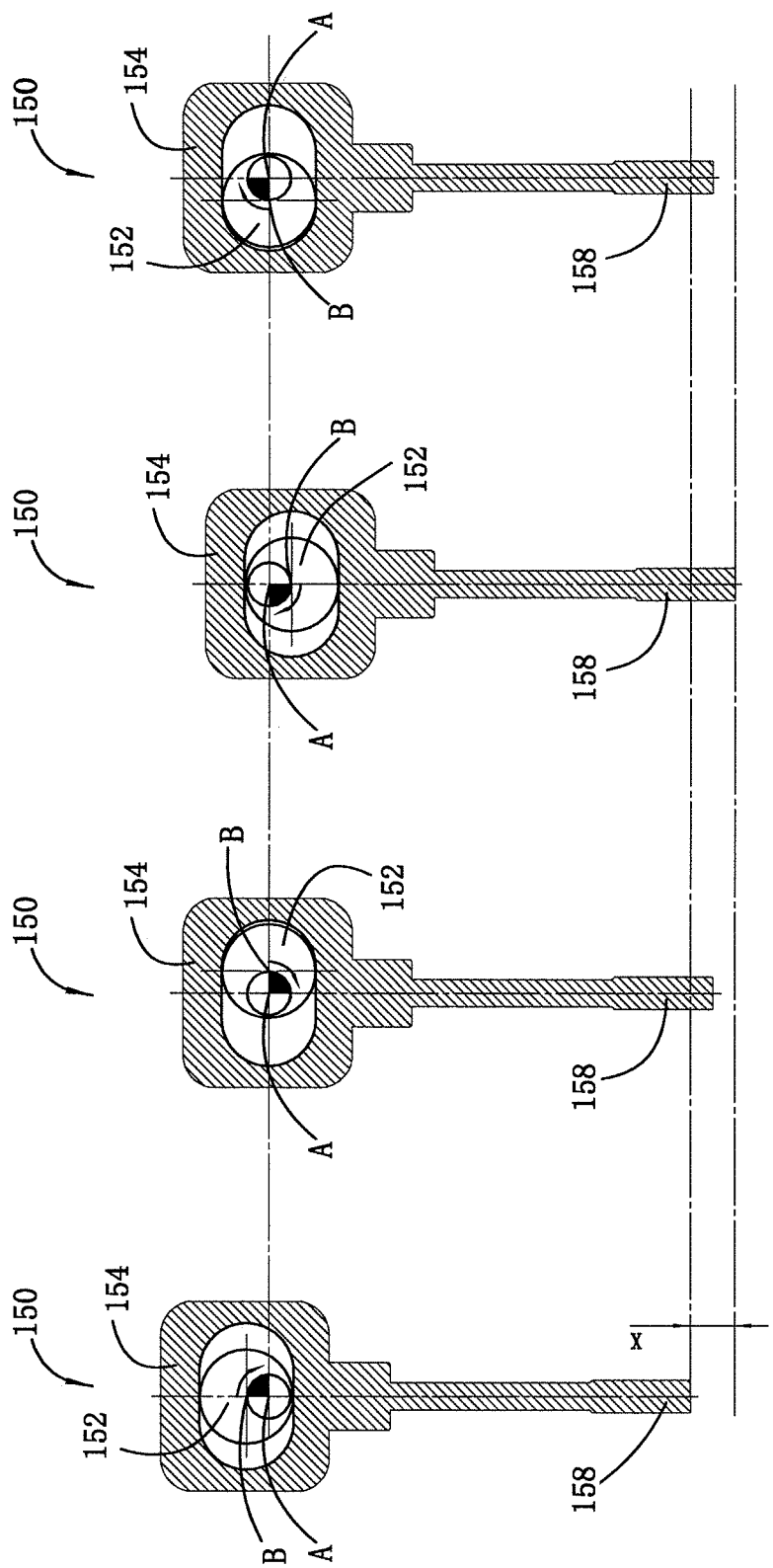

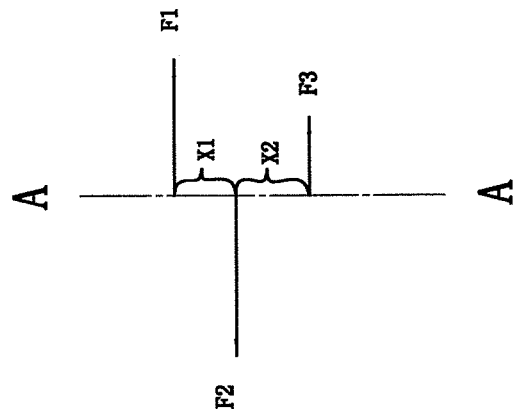
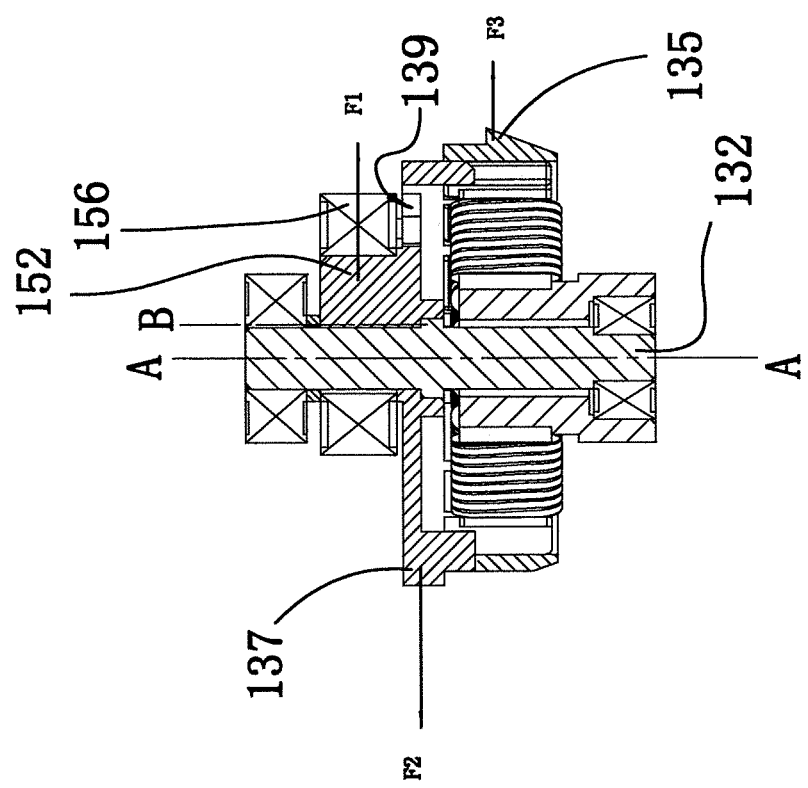
FIG. 13B
FIG. 13A

TATTOO DEVICE WITH MOTOR HAVING BUILT-IN MOTION CONVERSION MEMBER

FIELD

The present disclosure relates generally to tattoo devices, particularly to tattoo devices with rotary motor and motion conversion for converting rotary motion to translation motion.

BACKGROUND

Rotary tattoo devices typically include a rotary motor for reciprocally driving one of more needles to applying ink to the skin of a subject. The motor has a stator and a rotor supported in a motor housing. The rotor has a rotating shaft which is supported by bearings in the motor housing. A terminal end of the rotor shaft extends outside of the motor housing, and a rotary-linear motion conversion component, such as a cam or crank is coupled to the terminal end of the rotor shaft, for converting the rotary motion of the rotor shaft to reciprocal linear motion in order to actuate a needle shaft attached or connected to the needle(s).

For example, some conventional rotary tattoo devices and their respective arrangements of motor and needle assembly are disclosed in U.S. Pat. Nos. 5,551,319, 7,207,242, 9,827,409, 9,393,395, 9,662,483, and WO2014065726.

However, it is desirable to improve the existing tattoo devices, such as to simplify the construction and structure of the device, reduce vibration and wear-and-tear, or to improve lifetime of the device or its components including components of the rotary motor and motion conversion mechanism.

SUMMARY

Accordingly, an aspect of the present disclosure relates to a tattoo device. The tattoo device comprises a frame; and an actuator for actuating a needle-driving shaft. The actuator comprises an electric motor. The motor comprises a stator mounted to the frame, first and second bearings mounted to the frame, and a rotor. The rotor comprises a rotor shaft rotatably supported at the first and second bearings, and a motion conversion member for converting rotation motion of the rotor to translation motion for reciprocally actuating the needle-driving shaft. The motion conversion member is positioned between the first and second bearings. The actuator may comprise the frame. The tattoo device may comprise a housing, and the actuator and the needle-driving shaft may be housed in the housing. The frame may comprise a wall having first and second opposite sides, wherein the first bearing may be mounted to the first side of the wall, and the second bearing may be mounted to the second side of the wall. The first bearing may be mounted directly on the frame, and the second bearing may be mounted on the stator and indirectly to the frame. The stator may comprise a bushing fixedly mounted at the second side of the wall, the bushing comprising a recess or bore, and the second bearing may be mounted in the recess or bore. The motion conversion member may comprise a crank and a slotted slider coupled to the crank. The slotted slider may be coupled to the crank through a crank bearing. The motion conversion member may comprise a cam. The motion conversion member may comprise a slider-crank linkage or slider-crank mechanism. The motion conversion member may be fixedly mounted on the rotor, such as on the rotor shaft. The motion conversion member and the rotor may be integrated. The rotor may be shaped and configured to balance the weight of the motion conversion member so that a center of total gravity of the rotor and the motion conversion member is on or close to the rotation axis. The rotor may comprise a balancing portion for improving dynamic balance of the rotor and the motion conversion member, and thus reducing vibration caused by dynamic unbalance. The balancing portion may comprise at least one of a cavity or an added weight on the rotor. The electric motor may be a brushless direct-current motor. The stator may comprise stationary windings, and the rotor may comprise at least one magnet rotatable around the windings. The rotor shaft may be formed from a single rigid metal rod. The frame may be a unitary frame formed of a rigid metal. The frame may be a part of the housing. The frame may comprise a plurality of assembled frame components.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure:

FIGS. 10A, 10B, 10C, and 10D are schematic cross-sectional views of the crank, crank bearing, and slotted slider in the tattoo device of FIG. 1, at different rotation positions, illustrating movement of the slotted slider during operation;

FIG. 13A is a side cross-sectional view of the rotor of FIG. 8A;

FIG. 13B is a schematic force diagram showing centrifugal forces generated by rotation of the rotor:

DETAILED DESCRIPTION

Figure 1:
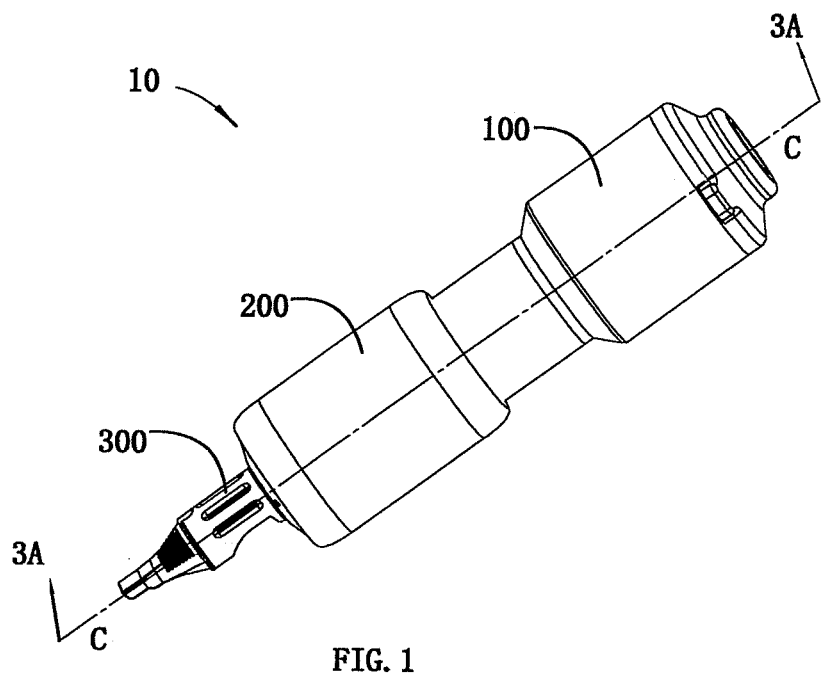
FIG. 1 is perspective view of a tattoo device, according to an embodiment of the present disclosure.
Figure 2:
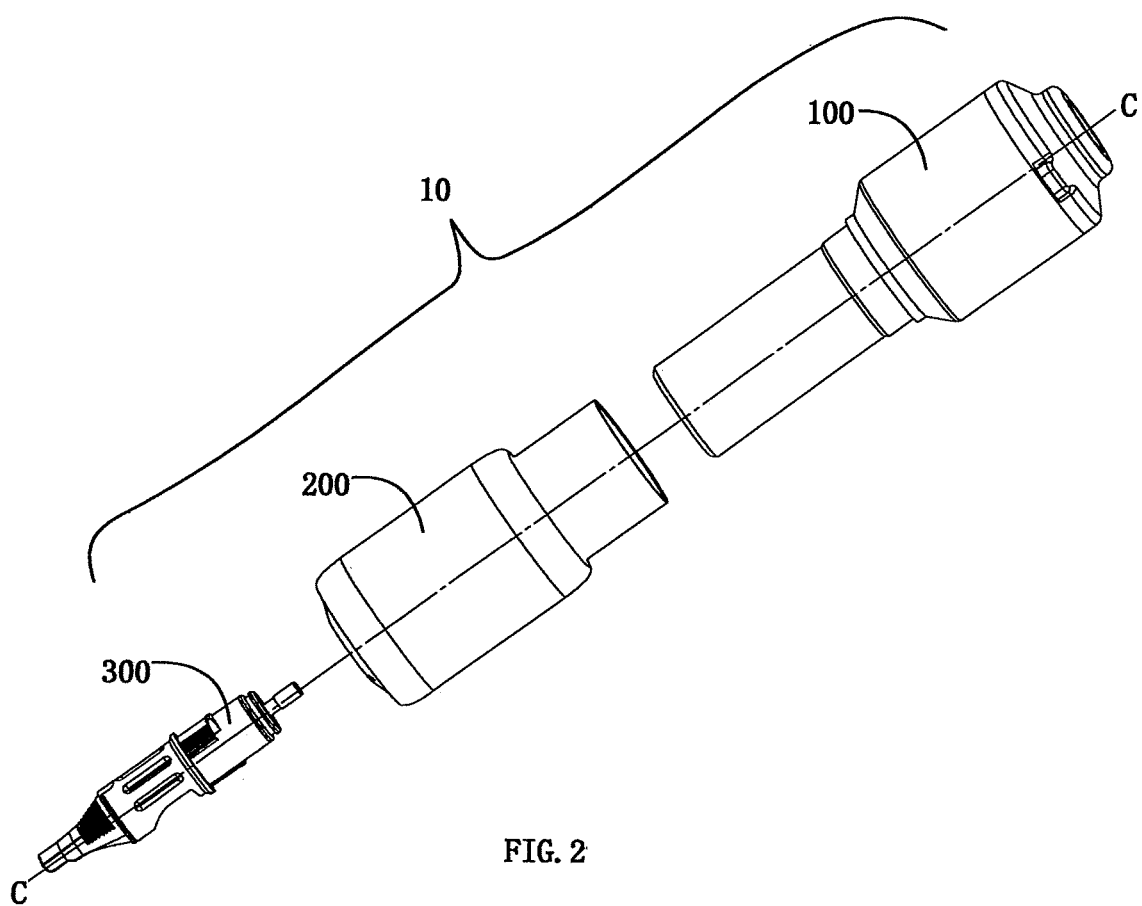
FIG. 2 is an exploded view of the tattoo device of FIG. 1.

In overview, in selected embodiments of the present disclosure in a tattoo device, a rotary motor with a built-in rotary-to-translation motion conversion member is provided. In particular, the motion conversion member is positioned and supported between bearings of the motor that support the rotor shaft of the motor.

It has been recognized that when a motion conversion mechanism is coupled to a terminal end of the rotor shaft outside the motor housing, as is the case in conventional rotary tattoo devices or machines, the terminal end of the rotor shaft is not supported on both sides of the motion conversion coupling, and can thus move radially or laterally (i.e. perpendicular to the axial direction of the rotor shaft) during operation. The load on the rotor shaft is also not born evenly by the two bearings. Most of the load is born by the bearing closer to the motion conversion coupling point. Consequently, the overhung load on the terminal end of the rotor shaft generated by interaction with the motion conversion mechanism is relatively high and produces a large force on the rotor shaft at the bearing nearer to the terminal end, and causes vibrations, which result in fatigue and wear-and-tear in the bearing over time, and reduces the lifetime of the bearing, or other components of the motor.

Conveniently, in embodiments disclosed herein, because the built-in motion conversion coupling member is located and supported between the two bearings of the rotor shaft, the rotor shaft is supported on both sides of the motion conversion coupling location, and the load produced by interaction with the motion conversion member is born more equally by both bearing. Consequently, both ends of the rotor shaft are restrained from radial motion by the bearings, and more smooth motion conversion can be achieved with reduced vibration and force applied to the rotor shaft. Further, the force/load applied to the rotor shaft is more evenly shared by the two bearings. As a result, wear-and-tear of the bearings and other motor components and the motion conversion coupling can be reduced and the lifetime of the motor and the bearings can be prolonged.

Also conveniently, with a motor with built-in motion conversion coupling, the combination of the motor and the motion conversion mechanism can be made more compact and takes up less room. Thus, more room may become available within the housing of the tattoo device to accommodate larger components including components of the actuator and other needle driving mechanism, particularly larger and more robust bearings.

It should be understood that these embodiments are only examples of many adventitious uses of the innovative teachings herein. In general, statements made in the specification of the present application to not necessarily limit any of the various claimed inventions. Moreover, some statements may apply to some inventive features but not to others. In general, unless otherwise indicated, singular elements may be in the plural and vice versa with no loss of generality. In the drawings, like numerals refer to like parts through several views.

An example embodiment of the disclosure is illustrated in the drawing. In particular, a tattoo device 10 is shown in FIG. 1. As depicted, tattoo device 10 is a handheld device, commonly referred to as a pen style tattoo device, tattoo pen, tattoo pen machine, pen tattoo machine, or the like.

Tattoo device 10 includes a base unit 100, a handle 200, and a needle module 300. The needle module 300 is connected to the base unit through handle 200. Base unit 100 is also referred to as a tattoo machine by itself. Base unit includes the actuation or driving components for actuating the movement of the needle, and may include the power source and controller for powering and controlling the operation of the tattoo device 100.

Handle 200 may be detachably connected to the base unit. In some embodiments, handle 200 and base unit 100 may be separately provided or sold. In other embodiments, handle 200 and base unit 100 may be provided and sold together. In some embodiments, handle 200 and base unit 100 may be provided as an integrated unit and not separable during use.

Handle 200 may be shaped and sized so it is convenient to be held in an operator's hand and used to perform tattoo operations. Handle 200 may be configured and constructed according to any suitable techniques, including those known to persons skilled in the art. An example handle as described in US 2019/0060626 by Xiao may be used. Other handles may also be used.

Needle module 300 may also be referred to as the needle cartridge, and contains one or more removable needles. An example needle module 300 is described in US 2019/0217072 by Xiao. The needle or needle bundle in needle module 300 may be reciprocally movable along the axis C, or in a direction parallel to axis C. The needle or needle bundle may be biased by an elastic member (not separately shown) in needle module 300 towards the handle 200. Needle module 300 has a coupling structure for engaging handle 200.

As the details of the handle 200 and needle module 300 are not the focus of the present disclosure, they will not be described further herein.

The description below focuses on the structures of the base unit 100.

Figure 3A:
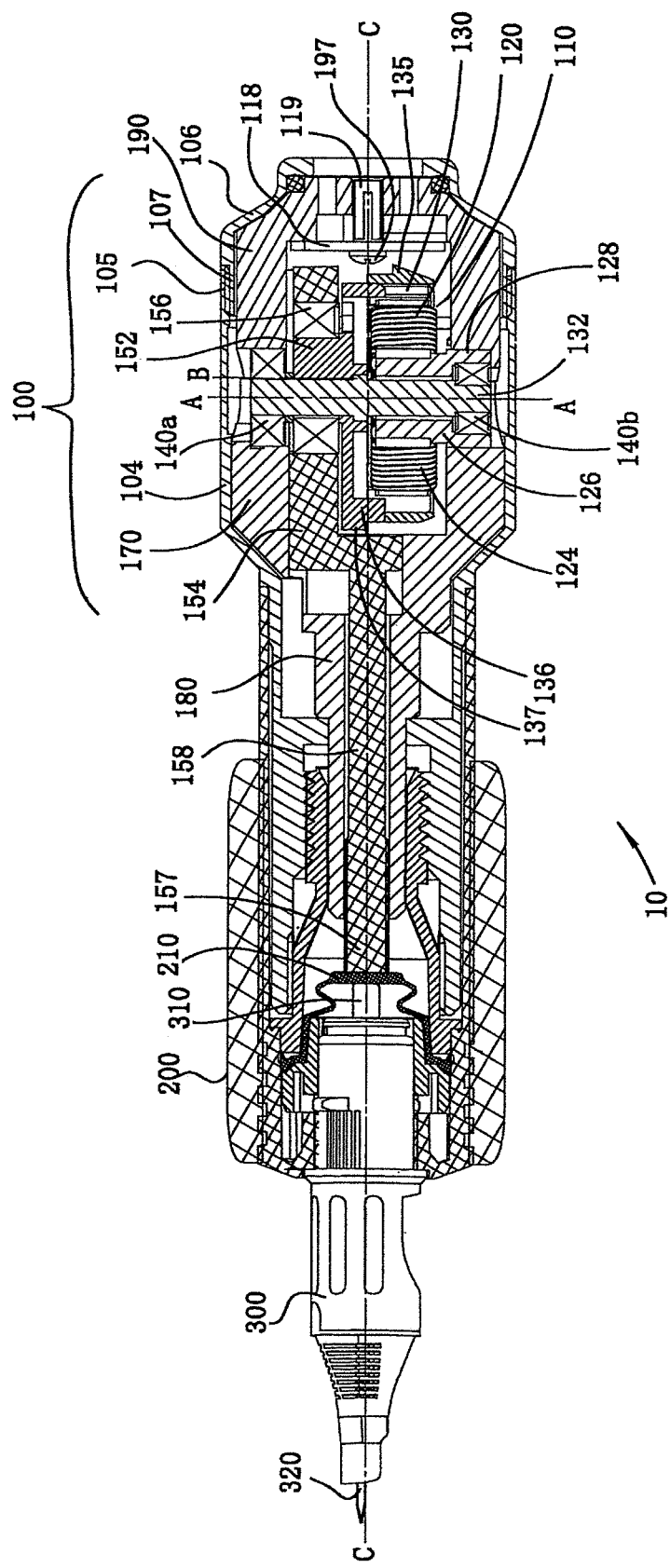
FIG. 3A is a cross-sectional view of the tattoo device of FIG. 1, viewed along line 3A-3A.
Figure 3B:
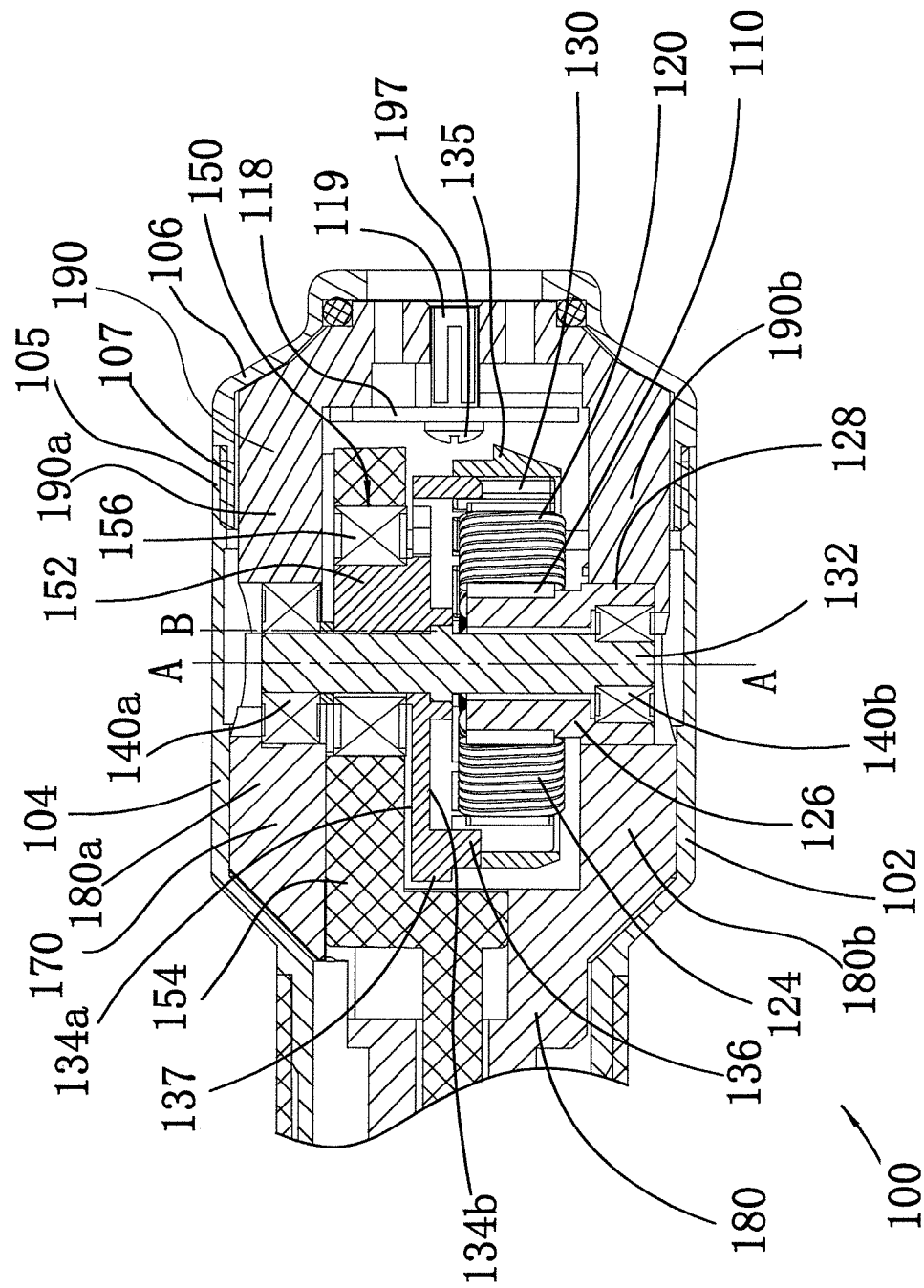
FIG. 3B is an enlarged cross-sectional view of the base unit of the tattoo device of FIG. 3A.
Figure 4:
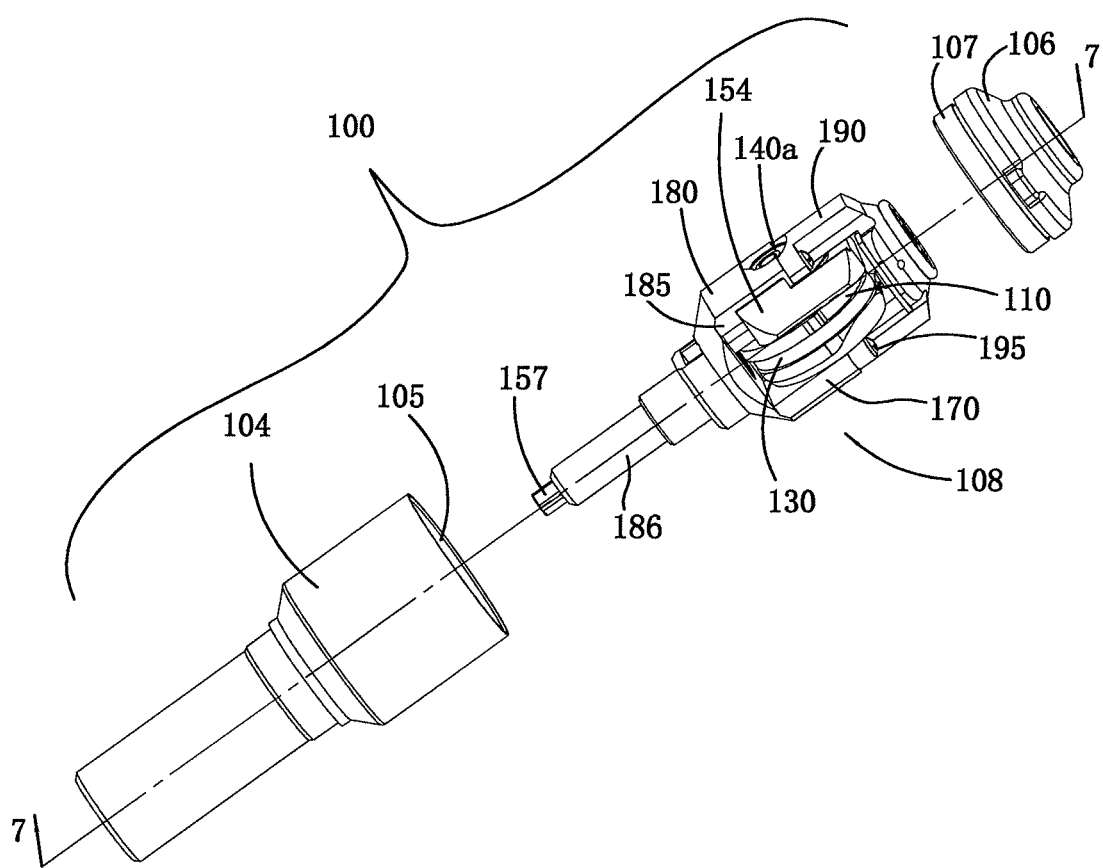
FIG. 4 is an exploded perspective view of the base unit of the tattoo device of FIG. 1.
Figure 6:
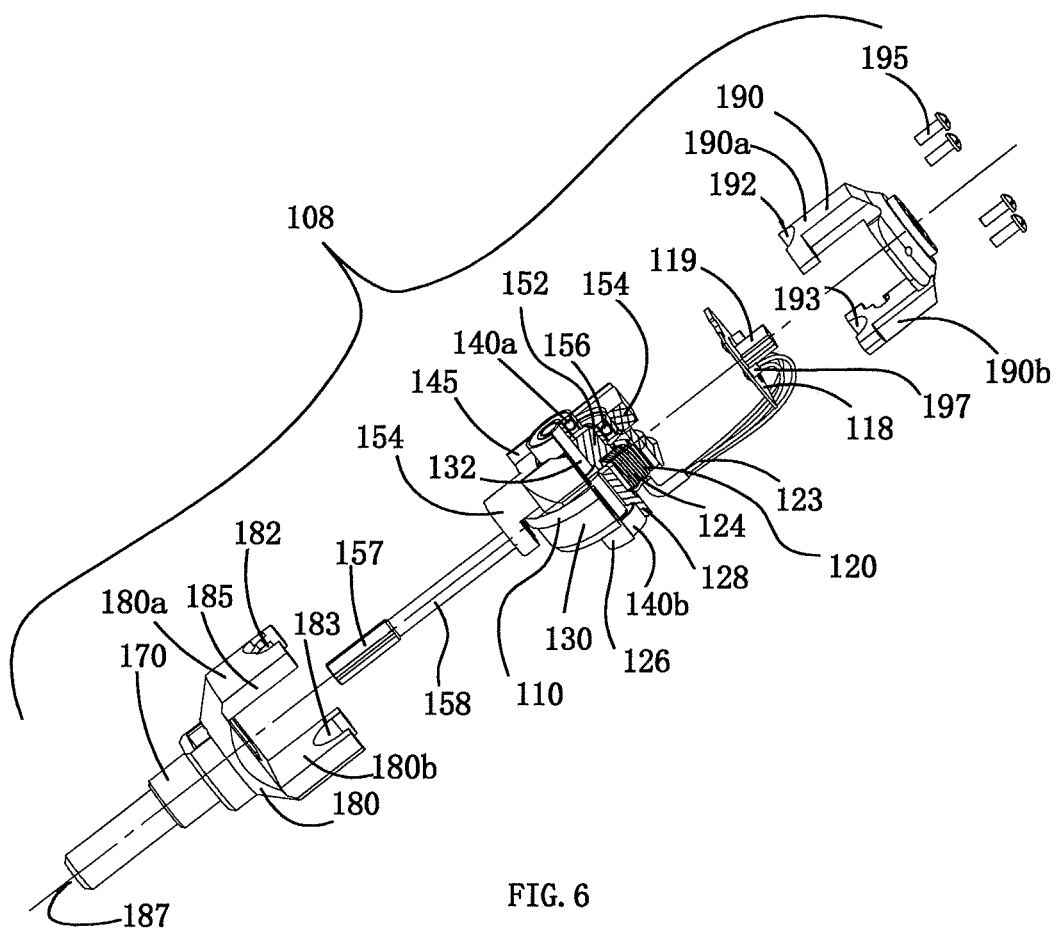
FIG. 6 is an exploded, partially perspective and partially cross-sectional view of the actuator of FIG. 5, where the motor is in an assembled state.

As better seen in FIG. 3B, FIG. 4 and FIG. 6 base unit 100 includes a housing 102. Housing 102 includes a generally tubular outer housing body 104 and a housing cap 106.

An actuator 108 is housed inside the housing 102.

The actuator 108 includes an electrical rotary motor 110.

The rotary motor 110 includes a stator 120, a rotor 130, bearings 140, and a built-in motion conversion coupling member 150. The rotary motor 110 may be constructed and operated according to a conventional technique for electrical rotary motors, except the inclusion of the motion conversion coupling member 150, and further changes made to accommodate and interact with the coupling member 150 as described herein.

Motor 110 is mounted on a frame 170. The frame 170 may include a lower frame portion 180 and an upper frame portion 190 coupled to each other, as depicted in the drawings.

In different embodiments, the frame 170 may be a unitary frame formed of a single piece of material, such as a rigid metal. Suitable materials for the frame 170 may include metal, such as an aluminum alloy. Example aluminum alloys include 7075 or 6061 aluminum alloy.

As can be better seen in FIGS. 3B, 3C, 5 and 6, each of the frame portions 180, 190 has two opposite sides, 180a, 180b and 190a, 190b respectively, which when assembled form frame walls for mounting various components of the motor 110, as will be further described below.

Rotor 130 includes a rotor shaft 132, supported at bearings 140a and 140b (also individually or collectively referred to as bearing 140). Bearings 140 are mounted at opposite sides of frame 170, or the walls formed by frame portions 180a, 180b, 190a, 190b respectively.

The rotor shaft 132 may be made of a single rigid metal rod. The rotor shaft 132 may be separately provided and mounted or attached to a rotor body 136. In some embodiments, rotor body 136 and rotor shaft 132 may be integrated and formed of the same material.

As illustrated in FIGS. 3A and 3B, the stator 120 is configured to produce a rotating magnetic field that alternately repels or attracts different magnets on the rotor 130 during operation and thus cause the rotor 130 to rotate along a rotation axis, such as the axis A as shown in FIG. 3A.

Figure 3D:
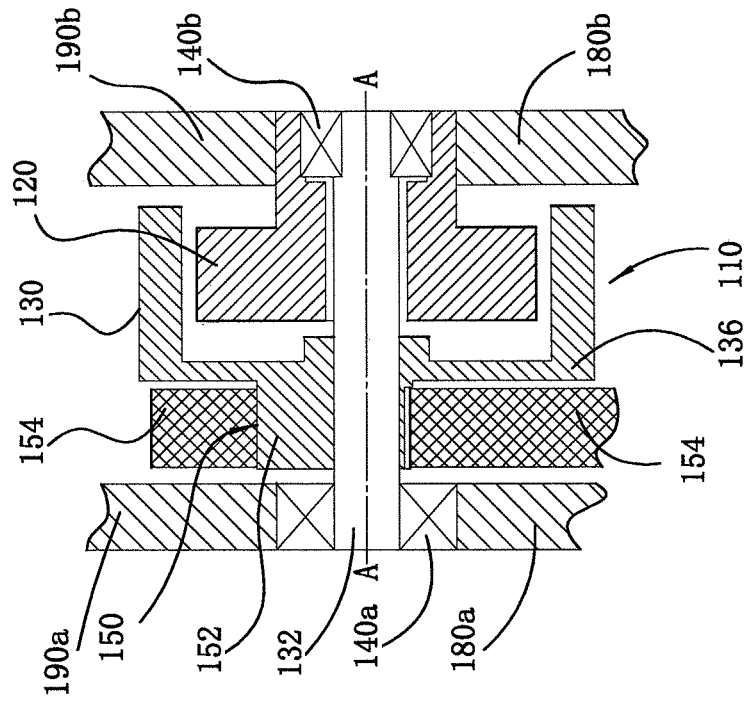
FIG. 3D is a simplified cross-sectional view of an alternative arrangement in the base unit.
Figure 3C:
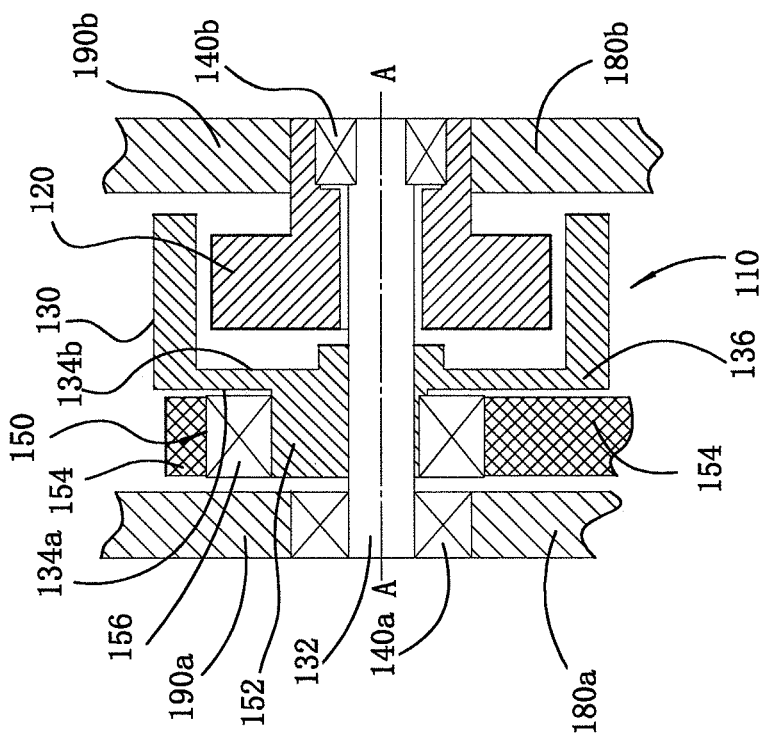
FIG. 3C is a simplified cross-sectional view of selected motor components in the base unit of FIG. 3B.

As better seen in FIG. 3C, rotor 130 has a first end face 134a and a second end face 134b.

A motion conversion coupling member 150, such as a cam or crank, is mounted on an end face of rotor 130, such as end face 134a as depicted in FIGS. 3A, 3B, and 3C. As depicted in FIGS. 3A and 3B, the motion conversion coupling member 150 includes a crank 152 and a crank bearing 156.

The crank conversion mechanism may include a crank-slotted slider mechanism as illustrated in the drawings and further explained below. The crank conversion mechanism may also include any suitable conventional crank linkages such a slider-crank linkage or a crank-slot linkage as known to those skilled in the art. In alternative embodiments, the crank coupling may include or be replaced by a cam coupling. It is noted that in the literature of tattoo machines and devices, a crank linkage is often also referred to as a cam linkage.

Crank 152 is configured, such as being fixedly mounted on or integrated with rotor body 136 of rotor 130, such as at the end face 134a or on rotor shaft 132, to rotate about axis A with rotor 130. Crank 152 may have a generally disc shape or the shape of a short cylinder and is coupled to a slotted slider 154, such as through crank bearing 156, so that when the crank 152 rotates, slotted slider 154 is driven to move translationally such as linearly in a direction substantially perpendicular to the rotation axis A. The central axis of crank 152 is off-set from the rotor axis A, and the crank 152 may be considered as an eccentric cam.

In some embodiments, as depicted in FIGS. 3A, 3B and 3C, a crank bearing 156 may be provided to rotatably couple the slotted slider 154 to crank 152 so that as crank 152 rotates, sliding friction in the crank linkage is reduced. When the rotor 130 rotates, crank 152 and crank bearing 156 will move in a circle around the rotor axis A, and a remote end of the slotted slider 154 will move in the direction "C" as seen in FIG. 3A, as will be further explained below with reference to FIGS. 3B, 3C, 3E and 10A-10D.

A simplified view of the arrangement in motor 110 is shown in FIG. 3C. Crank 152, slotted slider 154, and crank bearing 156 can function to convert rotation motion of the rotor to linear motion, similar to an eccentric-rod mechanism, as can be understood by those skilled in the art. The crank 152 functions as the eccentric, and the slotted slider 154 functions as the strap and rod in the eccentric-rod mechanism, but as will be further described below, slotted slider 154 differs from a conventional strap to avoid lateral motion that is present in a conventional simple eccentric-rod mechanism.

As better illustrated in FIG. 9A to 9D, the slotted slider 154 has a slot 155 and a shaft 158 with a sliding end portion 157. The slotted slider 154, particularly the sliding end portion 157 of the shaft 158, is axially coupled to the needle shaft 310 for reciprocally actuating the needle shaft 310. Slotted slider 154 may be in direct contact with needle shaft 310 or may be coupled to the needle shaft indirectly, such as through a soft sealing film 210 in the needle handle 200 as depicted in FIG. 3A.

The needle shaft 310 and the needle 320 in the needle module 300 can thus be driven along the axial direction C by movement of the slotted slider 154.

When the slotted slider 154 is driven to move towards the needle module 300 along axis C, the tip of the needle 320 extends out of the needle module 300 and can enter the skin of the subject to be tattooed. When the slotted slider 154 moves backward towards the top of the base unit 100, the needle 320 can retract into the needle assembly 300 by the biasing force provided in the needle module 300, as discussed above. For example, as disclosed in US 2019/0217072, the needle module 300 may have an internal mechanism for retracting the needle 320, such as an internal elastic band (not shown) suitably configured and mounted to bias the needle shaft 310 towards the handle 200. When the needle 320 is withdrawn into the needle module 300, it can come into contact with an ink stored in needle module 300. This process may be repeated to perform the tattoo operation.

The details on how the slotted slider 154 may be mechanically coupled with the needle shaft 310 are not the focus of this disclosure, and may be implemented with any suitable coupling structure or technique. Briefly, in some embodiments, a needle assembly such as needle module 300 may be operatively connected and coupled to the slotted slider 154 through handle 200, either directly or indirectly. The slotted slider 154 can function as a needle driving shaft, for driving the needle 320. The needle driving shaft is actuated to reciprocally move up and down during operation, and thus repeatedly drive the needle 320 from a retracted position towards an extended position. The needle assembly may include a mechanism to return the needle 320 from the extended position back to the retracted position when the needle drive shaft moves upward.

In addition to FIG. 3A, the base unit 100 is further illustrated in FIGS. 3B to 13D.

As can be better seen in FIGS. 3A and 4, the upper end of the outer housing body 104 has an inner threaded section 105, and lower end of the housing cap 106 has an outer threaded section 107. The threaded sections 105 and 107 are configured and sized to engage and couple with one another for attaching the cap 106 to the housing body 104 while enclosing the actuator 108 inside the housing of the base unit 100.

In different embodiments, housing body 104 and cap 106 may be removably coupled and attached to each other by a different coupling structure or mechanism or connectors, such as using key and keyway coupling or connectors, male-female connectors, snap locking, locking nut, locking pin, or the like, or a combination thereof. In some embodiments, the housing body 104 and cap 106 may be attached by welding, an adhesive, or a fastener. Suitable welding techniques may include soldering, arc welding, ultrasonic welding, or the like. In some embodiments, housing body 104 and cap 106 may be connected through frictional engagement such as with a tubing section and a sleeve section.

When housing body 104 and cap 106 are coupled and engaged, they define an internal chamber that houses the actuator 108, and may also house a portion of the needle drive shaft 158.

Figure 5:
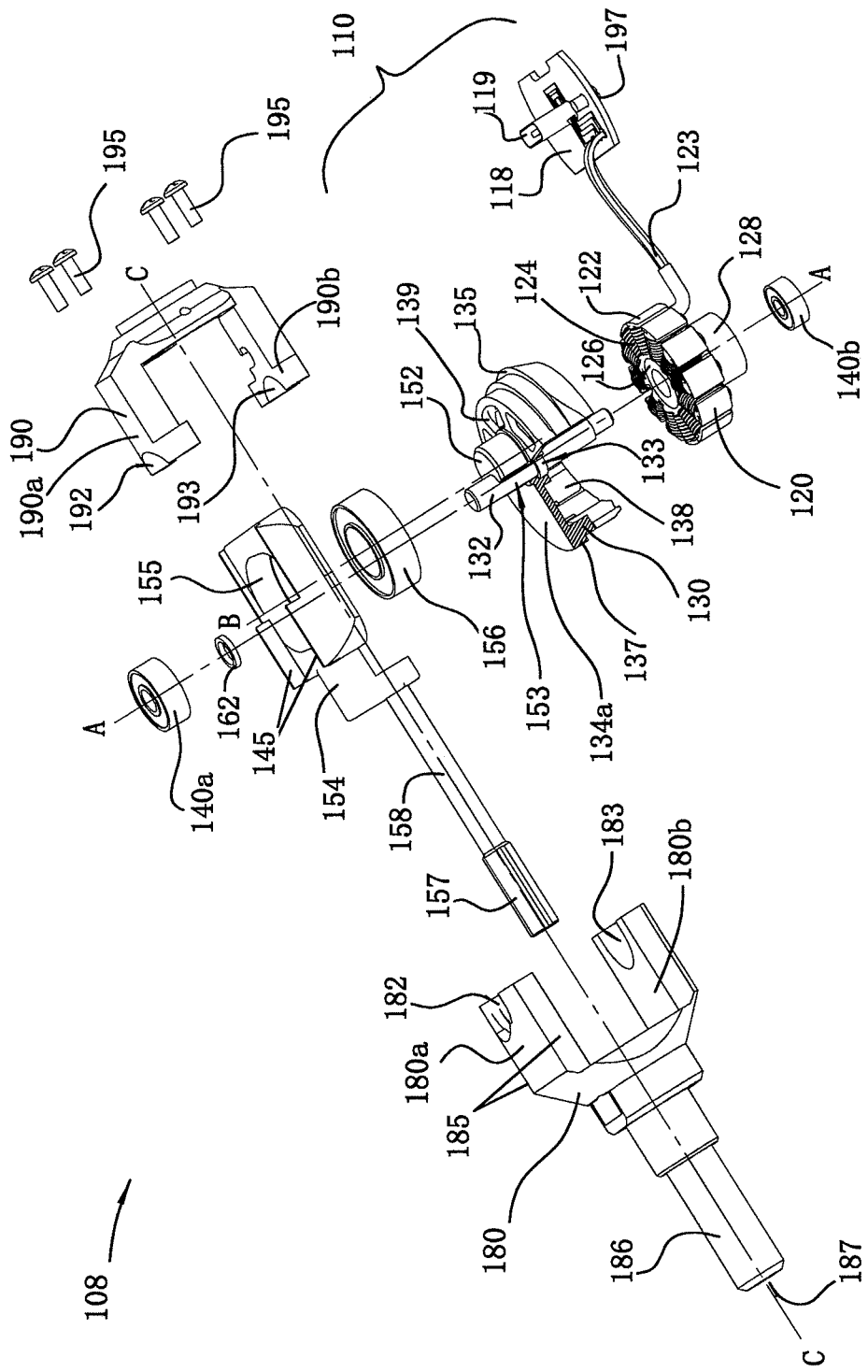
FIG. 5 is an exploded, partially perspective and partially cross-sectional view of the actuator in the base unit of FIG. 4.
Figure 7:
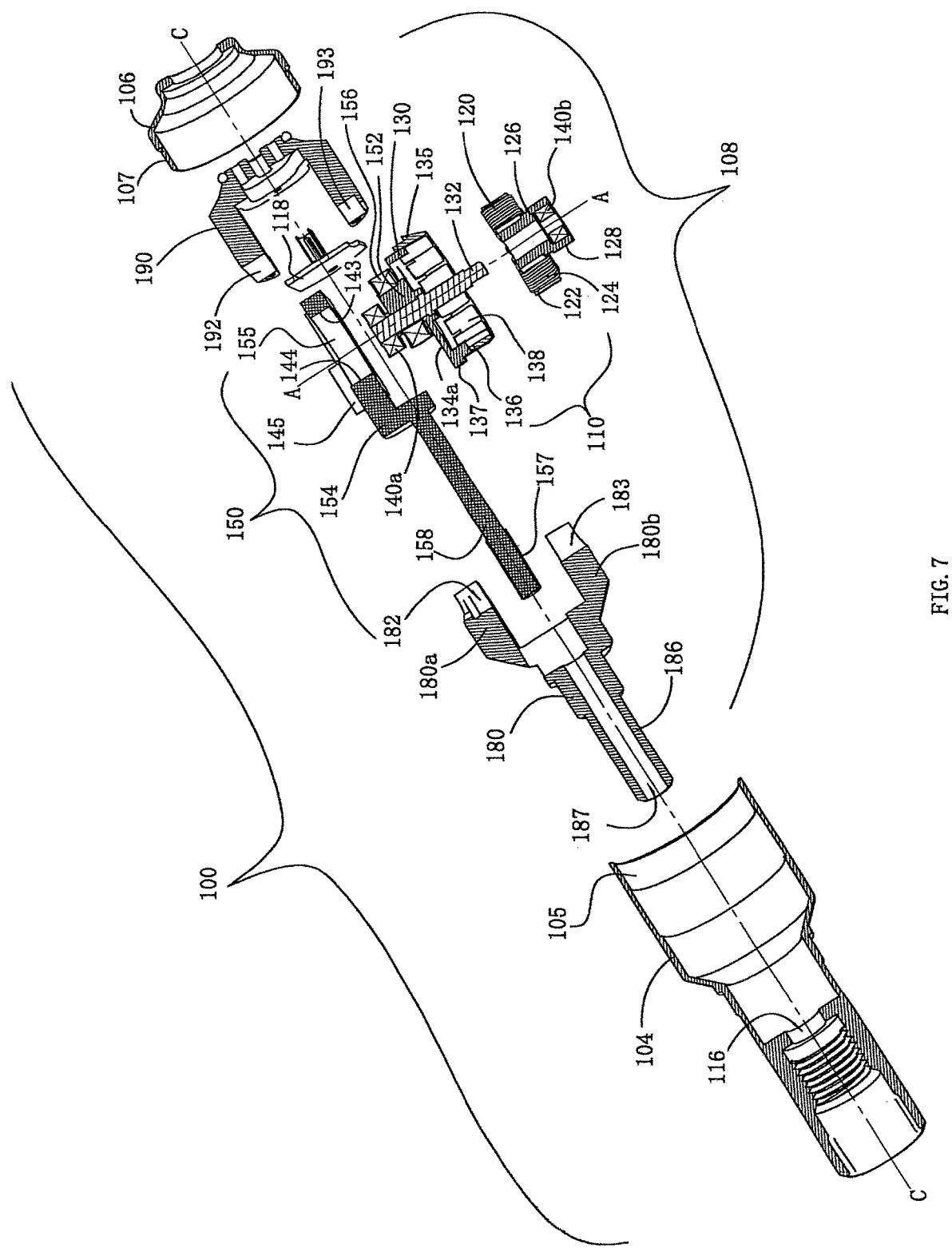
FIG. 7 is an exploded cross-sectional view of the base unit of FIG. 4, along line 7-7.

The actuator 108 is further illustrated in FIGS. 5-7 in addition to FIGS. 3A to 3D and 4.

FIGS. 5-7 illustrate specific embodiments of the actuator 108 and arrangements of the components of motor 110.

With references to FIGS. 3B to 3E and 4-8D, further details of the motor 110 are described next.

Motor 110 is an electrical rotary motor with a stator 120 and a rotor 130 as noted above. The motor 110 may be a brushless direct-current (BLDC) motor. As depicted in the drawings, the motor 110 may be an outrunner motor, where the stator 120 is an inner stator with fixed windings, and the rotor 130 is an outer rotor which has magnetic segments that are configured to rotate around the inner stator 120 during use. An outrunner motor may also be referred to as an external rotor motor, outer rotor motor, or a cup motor.

The mechanical, electrical and magnetic arrangements and operating principles of motor 110 can be the same or similar to those of any known electrical rotatory motors, which generally convert electrical energy into mechanical energy through electromagnetic interactions between the stator and rotor to produce rotation motion of the rotor.

The rotor shaft 132 of the rotor 130 is supported on bearing 140a and bearing 140b.

The motion conversion mechanism for converting rotary motion of the rotor 130 to translation motion of the needle drive shaft 158 may include the crank 152, crank bearing 156 and slotted slider 154, which provide a rotary motion to linear motion conversion mechanism.

In some embodiments, the crank 152 may be integrally formed on an end face of rotor 130, or on a portion of rotor shaft 132. In other embodiments, the crank 152 may be a separate component attached or affixed to the rotor 130, such as to the end face of the rotor 130 or a portion of the rotor shaft 132.

As can be appreciated, when the crank 152 and the rotor 130 are integrally formed, such as from a single piece of metal, there is no need to affix the crank 152 to the rotor by a fastener or other fastening or engaging device, so the actuator 108 can be more compact and have a smaller size. Further, it would be easier to assemble the device during use.

As can be appreciated by those skilled in the art, rotor shaft 132 may be integrally formed with other portion of rotor 130, but may also be separately provided and attached to the body of rotor 130 and crank 152 through a central shaft opening 133 in the rotor body 136, as depicted in FIGS. 3A-7. The rotor shaft 132 and the central shaft opening 133 have a close-fit engagement, and may be welded or glued, to prevent relative motion between the rotor shaft 132 and the rotor body 136. Similarly, crank 152 may have a shaft opening 153 through which the rotor shaft 132 is fixedly engaged with crank 152. In any event, when rotor 130 rotates, rotor shaft 132 and crank 152 also rotate at the same speed in the same rotation direction.

The stator 120 has windings 124, which may be configured and constructed according to any suitable technique including conventional stator technologies for outrunner motors.

Rotor 130 has magnetic segments 138, which may include permanent magnets. As depicted, the rotor 130 may have a tubular section with an inner wall, and the permanent magnets may be mounted on the inner wall of the tubular section of the rotor 130. In an outrunner motor, the rotor body 136 of rotor 130 may have a generally bell or cup shape, which may be referred to as the 'bell' or "cup" of an outrunner rotor. In some embodiments, magnetic segments 138 may be replaced with a magnetic ring (not shown) as can be understood by those skilled in the art.

It is noted that while other types of motor may be used in actuator 108, an outrunner motor may provide some performance benefits or advantages in at least some applications. For example, a larger rotor may be accommodated within the same motor housing or for a motor having the same overall size when the motor is an outrunner motor, as compared to a motor with an inner rotor. Further, the weight distribution of the outrunner rotor favors towards the outer perimeter of the rotor, thus providing a larger rotation momentum and a larger rotational inertia. A larger rotational inertia of the rotor can help to dampen negative effects such as torque ripple, which is a problem in motors with an inner rotor, can provide more smooth and more stable operation, even at relatively low speeds, such as at rotations of 1500 rpm.

It is noted that the torque ripple effect may be significant or increased when the load applied to the rotor changes periodically during rotation, such as when a cam or crank is coupled to the rotor or rotor shaft to convert rotary motion to linear or translation motion. Thus, it is particularly helpful in such cases to take care to reduce the torque ripple effect.

Another possible advantage of using an outrunner motor is that the rotation torque produced by the motor can be larger as compared to motors of the same size but with a smaller inner rotor. In particular, the rotation torque provided by the rotor 130 is proportional to the magnetic force experienced by the magnetic segments of the rotor 130 and the distance (or the radius) between the magnet segments and the central axis A. The larger the magnetic force and the distance (radius), the stronger the torque. For a given motor size, the air gap area between the stator and the rotor can be larger in an outrunner motor as compared to an inner rotor motor, and a larger air gap allows a stronger magnetic force to be applied. Further, the magnetic segments on the rotor of an outrunner motor would have a larger radius as compared to those of an inner rotor motor, and thus produces a larger torque at the same rotation speed. When the rotor rotates around the stator, the increased diameter and space also allows more magnetic segments (poles) to be provided on the rotor, which also increases the magnetic flux and the magnetic force that can be applied to the rotor.

Considered from another perspective, to provide the same torque or similar performance, an outrunner motor can be constructed with a smaller axial size in the axial direction. A compact motor or actuator with relatively high torque and smooth, steady rotation speed is desirable in tattoo devices, particularly hand-held tattoo devices or machines including pen-style tattoo devices.

In some specific embodiments, the stator 120 may include a multiphase winding 124 on a laminated stack 122. The laminated stack 122 is fixedly mounted to a stator bushing 126. The stator bushing 126 has a mount end 128 fixedly mounted to the lower frame portion 180b at the mount end recess 183.

The upper frame 190 and the lower frame 180 may be connected and secured to each other using threaded bolts 195. Bolts 195 may be tightened to apply pressure to securely connect upper frame 190 and lower frame 180.

The bolts 195 are respectively received in the mount end recesses 193 of the upper frame 190 and the mount end recesses 183 of the lower frame 180, for secure the mount end 128 by pressure.

The rotor 130 may include a number of N-pole and S-pole permanent magnet segments 138, or a molded magnetic ring. The rotor 130 may also include a rotor body 136 which has a generally bell or cup shape, and is formed a steel or iron material. The magnetic segments 138 are affixed to the inner surface of the rotor body. The rotor 130 has a central rotation shaft 132.

A number of N-pole and S-pole Permanent magnet segments 138 being annular and circumference surrounding shaft 132 (and also being annular and surrounding winding 124 and laminated core 122 of the stator 120).

The rotor shaft 132 is rotatably supported by a first bearing 140a at a first end of the rotor shaft 132 and supported by a second bearing 140b at a second end of the rotor shaft 132. That is, rotor shaft 132 is supported at its opposite ends by two bearings 140 respectively.

The bearings 140 may be ball bearings. An advantage of using ball bearings is that there is low friction during rotation. Further, ball bearings produce lower noise as compared to some other bearings such as friction sleeve bearings. These factors may be of concern when using a high speed motor in a tattoo machine or device.

The first bearing 140a is supported by the lower frame portion 180a of lower frame 180 at bearing recess 182, and is secured in place between bearing recess 182 and bearing recess 192 by coupling of the upper frame 190 and the lower frame 180 with the pressure applied by the bolt 195. The first bearing 140a is thus fixedly mounted relative to the frame 170 during operation.

The second bearing 140b is supported by the stator bushing 126 at the mount end 128. The stator bushing 126 is fixedly mounted on the lower frame portion 180b and so the second bearing 140b is also fixedly mounted relative to the frame 170, albeit indirectly.

As can be understood by those skilled in the art, the stator windings 124 may be connected to an electrical power source to provide the needed electrical current through the windings for operation. The current in the stator windings 124 may be controlled in magnitude and sequencing (commutated) to effect rotation of the rotor 130, in a similar manner as in a conventional brushless motor.

Figure 8A:
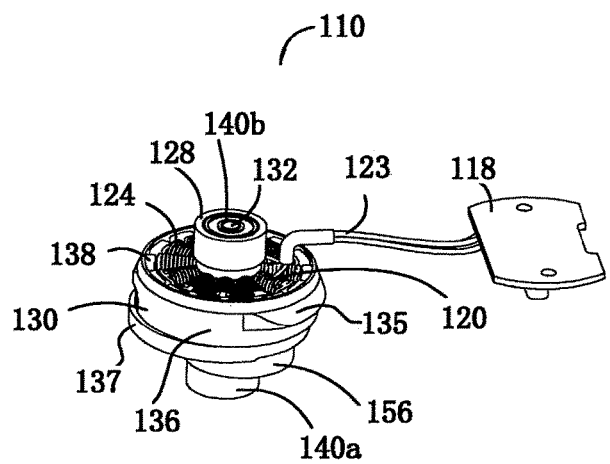
FIGS. 8A, 8B, 8C, and 8D are perspective views of a motor assembly used in the tattoo device of FIG. 1, with a stator, a rotor, and a motion conversion coupling.
Figure 8B:
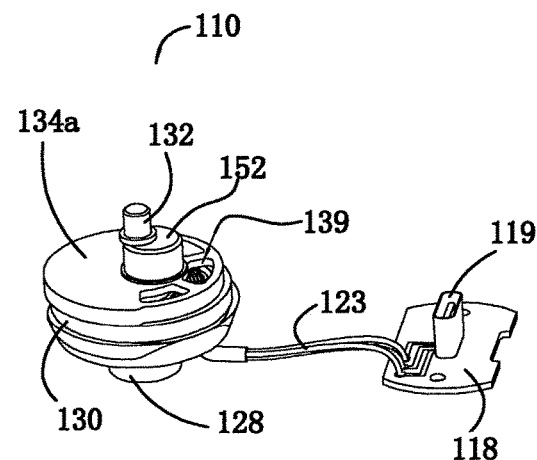
Figure 8C:
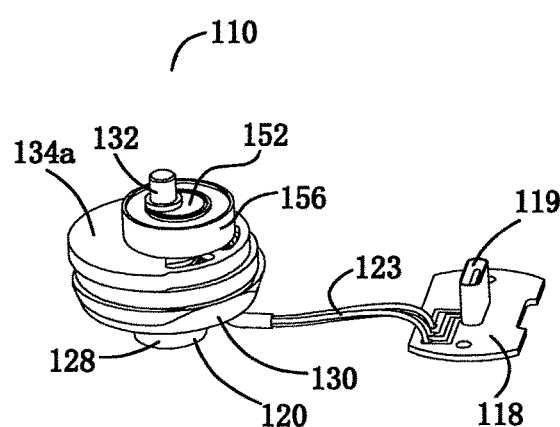
Figure 8D:
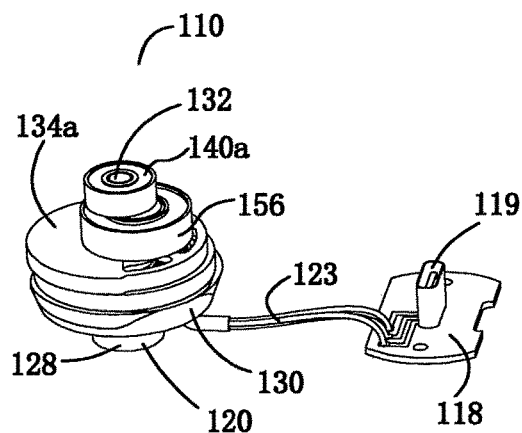

For example, as illustrated in FIGS. 8A-8C, the windings 124 of stator 120 may be connected to an electrical connector board 118 by electrical cable 123, and electrical power may be provided to stator 120 through an electrical connector 119 on the electrical connector board 118 from or by a motor control unit or a motor power supply (not shown), such as using an elongated flexible electrical cord (not shown).

The board 118 may be mounted on the frame 170, such as upper frame 190, using bolts 197 as illustrated in FIGS. 3A, 3B, 5 and 6.

The rotor shaft 132 has a longitudinal rotation axis A.

In different embodiments, the crank 152 may be cylindrical. When crank 152 is cylindrical as depicted in the drawings, the cylindrical crank has a central axis B that is off-set from rotor axis A, so crank 152 is eccentric or non-coaxial with respect to the rotor axis A.

In some embodiments, crank 152 is integrated with the rotor body 136, and is positioned at an end face of rotor body 136 as depicted in FIGS. 3C and 3D. The crank 152 and rotor body 136 may be a unitary component.

Alternatively, the crank 152 may be separately produced or formed, and then mounted, affixed, or coupled to the rotor 130, such as to or on the rotor body 136 or the rotor shaft 132 by a suitable method such as using glue, a fastener, or welding.

As depicted in FIGS. 3B, 3C, and 5, with a generally circular and cylindrical crank 152, the motion conversion coupling 150 may further include a crank bearing 156 around the crank 152 so that crank 152 can rotate within crank bearing 156. Crank bearing 156 may be a ball bearing.

Figure 3E:
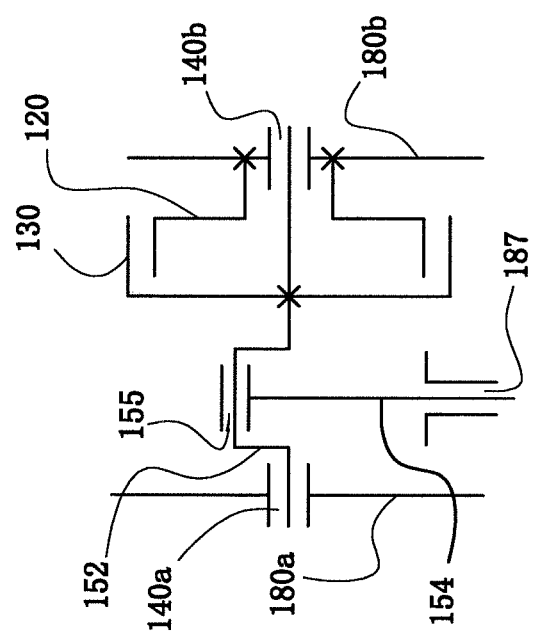
FIG. 3E is a schematic line diagram illustrating the relative arrangement of the components in the base unit of FIG. 3B.
Figure 11:
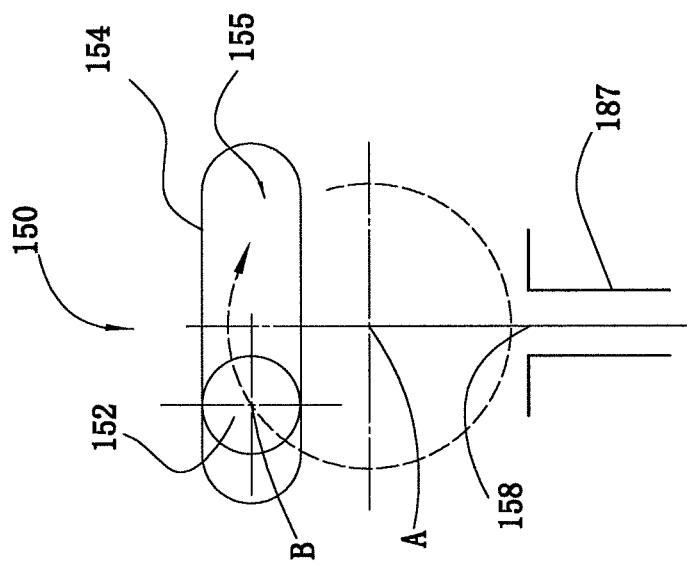
FIG. 11 is a schematic line diagram illustrating the relative movement of the crank, slotted slider and crank bearing of FIGS. 10A-10D during rotation.

As schematically illustrated in FIGS. 3E and 11 (also see FIG. 3C), when rotor 130 rotates about motor axis A, crank 152 and crank bearing 156 translationally move around a circle about the motor axis A. Crank bearing 156 also rotates about its own central axis and the central axis B of crank 152. The rotation of crank bearing 156 about its own axis allows relative rolling contact among the components of the crank linkage, and reduces friction caused by relative sliding motion between the contacting surfaces.

Figure 9A:
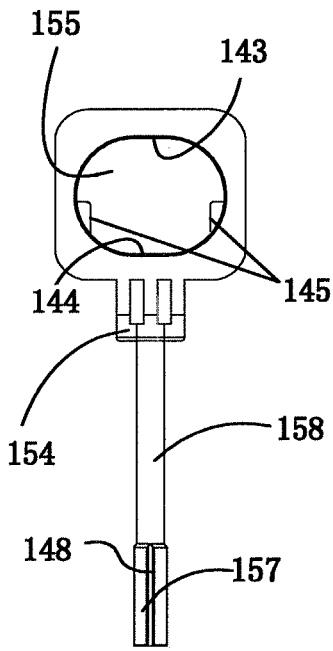
FIG. 9A is a front plan view of a slotted slider for use in the tattoo device of FIG. 1.
Figure 9B:
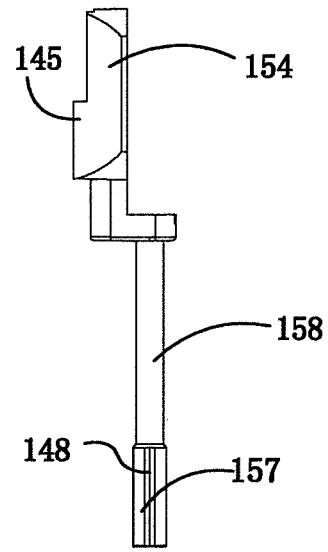
FIG. 9B is a left side plan view of the slotted slider.
Figure 9C:
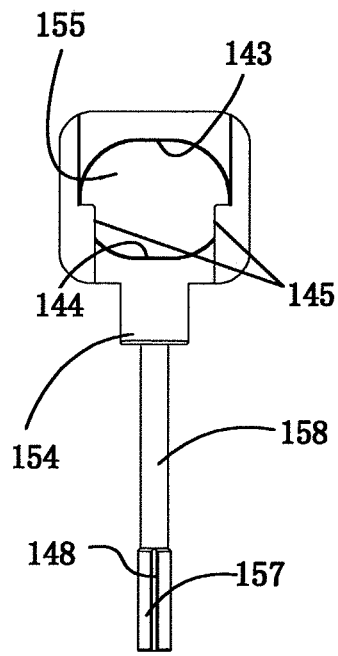
FIG. 9C is a rear plan view of the slotted slider.
Figure 9D:
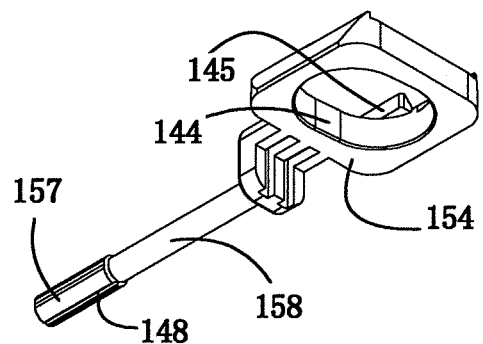
FIG. 9D is a perspective view of the slotted slider.

As will be further described below with reference to FIGS. 9A-9C, the crank bearing 156 is coupled to slotted slider 154, and the circular translational motion of the crank 152 and crank bearing 156 about the axis A is converted to linear translational motion of the slotted slider 154 for driving the needle 320.

The crank-crank bearing-slotted slider structure as depicted in the drawings can provide smooth motion conversion with low motion friction between the components of the structure, which may conveniently have a relatively long service life. The crank bearing 156 may have ball bearings. In particular, with this structure, there is no sliding engagement between the crank 152 and the slotted slider 154. Moreover, the crank bearing 156 may be a lubricated and sealed bearing, in which case, the use of the crank bearing allows dry, lubrication-free engagement between the crank 152 and the slotted slider 154. As a result, the tattoo device does not require extensive, frequent maintenance. A liquid lubricant is also not required in the motion conversion coupling, so it is easier to keep the base unit 100 clean.

In different embodiments, the crank bearing 156 may be a different type of bearing, such as roller bearing, needle bearing, or the like.

As can be better seen in FIGS. 9A-9D, the slotted slider 154 has an upper end with a slot 155, and a shaft 158 with the sliding end portion 157 at the lower end, which is configured to slide along a sliding track. Shaft 158 connects the upper end and the lower end. The slot 155 is shaped and sized for receiving and coupling with the crank 152 through crank bearing 156. For example, the slot 155 may have a generally rectangular shape but with a semicircle at each lateral end, where the radius of the semicircles (and hence the width of the slot 155) is about the same or slightly larger than the radius of the crank bearing 156, but the length of the slot is larger than the diameter of the crank bearing 156 and is larger enough to allow the crank bearing 156 to laterally move within the slot 155 without touching the semicircular ends during a full circle, so that the crank bearing 156 can move laterally within the slot 155 as the crank bearing 156 is circling around axis A, but will keep in contact with edges 143 and 144 of the slot 155 to cause the slotted slider 154 to move up and down.

As a result, the rotation of the rotor 130 causes circular motion of the crank 152 and crank bearing 156, which, in turn, causes linear motion of the slotted slider 154.

The slotted slider 154 is actuated by the crank bearing 156, and functions similar to a crank arm.

The slotted slider 154 may be coupled to, or integrally formed with, the needle drive shaft 158.

The shaft 158 has a sliding end portion 157, which is sized and shaped to slide smoothly in the slider guide 187 of the lower frame 180.

The sliding end portion 157 may have one or more grooves 148 extending along the axial direction to all air communication through the grooves 148. Air communication through grooves 148 prevents build-up of air pressure on either end of the sliding end portion 157 due to reciprocal motion. The grooves 148 may also be useful to store a lubricant therein to reducing sliding friction and allow more smooth sliding motion of the sliding end portion 157 in the sliding track.

The shaft 158 and the sliding end portion 157 may be integrally formed from the same material. The entire slotted slider 154 may also be integrally formed from the same material.

To prevent sliding end portion 157 to rotate around the axis C, the slotted slider 154 may include a keyway formed of opposing keyway surfaces 145. Keyway surfaces 145 abut the key surfaces on a frame panel 185 in the lower frame 180 when assembled, thus preventing rotation of the slotted slider 154 around the axis C.

The lower frame 180 includes two frame panels 185. One of the frame panels 185 forms a key having key surfaces that couple with the keyway surfaces 145 of slotted slider 154 to guide the slotted slider 154 to slide along the axis C, and limits rotation of the slotted slider 154 about the axis C. The lower frame 180 also includes a tubular dowel 186 for positioning and connecting the lower frame 180 to the outer housing body 104, which has a correspondingly sized dowel hole 116 (see FIG. 7) for receiving and engaging the dowel 186. The open channel or through hole in the tubular dowel 186 forms a slider guide 187 (or slider track), for receiving and guiding the sliding end portion 157 to slide in the guide 187. When assembled, the shaft 158 with sliding end portion 157 can extend into the handle 200 to drive the needle shaft 310 through handle 200, as illustrated in FIG. 3A. As can be appreciated, slotted slider 154 moves only up and down along axis C during operation.

As illustrated in FIG. 10A to 10D, during operation, the outer ring of the crank bearing 156 moves in a circle about axis B and pushes the slotted slider 154 to move up and down with a sinusoidal motion pattern in its moving speed.

Specifically, when the rotor 130 is rotated to the position as shown in FIG. 10A, the crank 152 is at the highest point above the rotor axis A. Correspondingly, crank 152 and crank bearing 156 pushes the slotted slider 154 to the highest point. When the rotor 130 is rotated 90° clockwise to the position as shown in FIG. 10B, the crank 152 is moved to the right most point. As the opening in the frame of the slotted slider 154 allows the crank 152 to move towards the right laterally, the slotted slider 154 does not move laterally but is lowered to the middle point vertically. When the rotor 130 continues to rotate clockwise by 90° to the position shown in FIG. 10C, the crank 152 is at the lowest point, pushing the slotted slider 154 to the lowest point as well. When the rotor 130 is further rotated 90° clockwise to the position as shown in FIG. 10D, the crank 152 is moved to the left most point, and the slotted slider 154 is consequently moved by the crank bearing 156 to the mid-point in the vertical direction. Slotted slider 154 thus moves up and down but does not move left and right, as illustrated in FIGS. 10A-10D.

The movements of the axis B of the crank 152 and slotted slider 154 during rotation of the rotor 130 can be better understood from the schematic diagram shown in FIG. 11, which tracks the movement of axis B and shows the direction of movement of the slotted slider 154 during rotation.

At any given moment, there is only one pressure point or a small contact area between the crank bearing 156 and the slotted slider 154 that applies the actuating force to the slotted slider 154. The crank bearing 156 can roll along the inner surface of the slot 155 of the slotted slider 154.

Thus, the eccentric or non-coaxial offset of the central axis of the crank 152 and the crank bearing 156 lead to up and down motion of the slotted slider 154 and the needle drive shaft 158 when the rotor 130 is rotating, without lateral movement of the slotted slider 154.

Thus, the needle shaft 310 and needle 320 are driven by rotation of the crank 152 in a generally linear direction. The back and forth motion of the needle 320 punctures the top layer of the skin and drives insoluble particles of ink into the dermal layer of skin.

As can be appreciated, the force acting on the needle draft shaft 158 originates from rotation of the rotor 130, through the motion conversion coupling members including crank 152, crank bearing 156, and slotted slider 154.

As the motion conversion coupling components are supported between motor bearings 140a and 140b, the load is evenly born and shared by the two bearings 140, and both ends of the rotor shaft 132 are stable during operation. The ends of rotor shaft 132 will not oscillate during operation like an unsupported cantilever end would do.

In comparison, if a cam or crank is coupled to a free end (or cantilever end) of a motor shaft outside the motor housing as in some conventional tattoo machines, the load force acting on the cam or crank and the needle drive shaft will be born mainly by the motor bearing that is closest to the cam or crank, and the free end of the motor shaft would oscillate or vibrate substantially during operation. The large load on the bearing and the vibration would generate fatigue in the motor bearing, which may result in damage in the motor over time, or malfunctioning of the tattoo machine.

While a crank-slotted slider structure is depicted in the drawings, other types of motion conversion mechanisms and structures may also be used. For example, a cam or crank may be coupled to the rotor shaft or rotor body. The cam or crank coupling or linkage may have different shapes and sizes. Some motion conversion mechanisms and principles generally disclosed in the literature may be adapted and reconfigured to be integrated with the motor 110 according to the present disclosure. For example, U.S. Pat. Nos. 5,551,319, 9,393,395, and WO2014065726 disclose different motion conversion mechanisms, which may be modified and used in an embodiment of the present disclosure.

In some embodiments, a crank-slider mechanism may be used to convert rotary motion into linear or translation motion.

The crank-slider mechanism may include a crank coupled to the rotor and a slider attached to the crank or connected to the crank by a connecting rod. The crank mechanism (e.g. the slider) is then coupled to the needle drive shaft.

Alternatively, the crank mechanism may be directly coupled to the needle, without a separate drive shaft. Or in other words, the connecting rod of a crank-slider mechanism may be the needle driving shaft. A guide frame may be provided in the handle or in the frame of the base unit for guiding the movement of the driving end of the connecting rod. For example, a crank coupling as disclosed in U.S. Pat. Nos. 5,551,319, 7,207,242, 9,827,409, or 9,662,483, may be modified and used in an embodiment of the present disclosure.

In some embodiments, the rotor 130 and the motion conversion coupling 150, such as crank 152 and crank bearing 156 may be weight-balanced to reduce vibration and other negative effects of un-balanced weight distribution due to the incorporation of the motion conversion coupling members into the motor 110.

As can be understood by those skilled in the art, when an unbalanced weight mass is rotating about an rotation axis, the rotating mass can exert linear and torsional forces on the rotation support that are periodically changing in direction, although generally perpendicular to the axis of rotation. Such periodic changes cause vibration of the rotation system, and can have negative effects on the system and reduce the lifespan of the system. In particular, a support bearing that supports the rotating mass and is subjected to such periodic load changes and vibrations may have reduced service life. A torsional force or an instantaneous linear force applied to the bearing can cause early failure of the bearing.

Unbalanced rotation and vibration can also produce noises and make the device uncomfortable to use when held in the hand by the user during operation. Further, vibration makes it more difficult to draw lines or touch specific points on the skin accurately. Long term use of a vibrating device may also cause hand or finger numbness.

These problems with unbalanced rotation systems are generally worse when the rotation speed is high, such as at 6000 to 9000 rpm, which is a typical range of rotation speed for many tattoo machines.

To avoid vibration and the above noted problems associated with unbalanced weight distribution, the rotor 130 and motion conversion coupling member 150 may be weight balanced in some embodiments of the present disclosure.

For example, one or more weight balancing members may be mounted on the rotor 130 to counter-balance the weight and load produced by the motion conversion coupling member 150.

It is also recognized that that weight balancing has two aspects, the static balance and the dynamic balance.

Static balance aims to move the center of gravity of the mass to the center of rotation, by balancing the weight distribution. In the present example as illustrated in the figures, static balance can be achieved when the center of gravity of the entire weight load supported by the rotor shaft 132 and the bearings 140 is on the rotation axis A. Under the static balanced condition, the weight is balanced with respect to the axis A when the rotor 130 is at rest. In practice it may not be possible to match the center of gravity and the axis A exactly, but as long as they are closer enough, the static balance may be satisfactory for the given application. Static balance may be achieved by adding counter-balancing weight, or redistributing existing weight, or both.

A simple method to determine if the system is static balanced is to test if the rotor 130 can stay at rest in any rotational position when the rotor shaft 132 is horizontal.

Dynamic unbalance occurs when the central principle axis of the total mass of the rotor 130 and motion conversion member 150 does not align with the rotation axis A of the rotor 130.

Dynamic balance aims to align the central principal axis with the rotation axis, so as to reduce or minimize any centrifugal forces or couple experienced by the system during rotation of the rotor 130. To achieve dynamic balance, one or more balancing portions may be provided on rotor 130. The balancing portion may include added counter-balancing weight at selection locations, or cavity (reduced weight) at selected locations, or both. Supported components may also be redistributed along the rotor shaft 132 to adjust the direction of the central principle axis.

For example, if a rotating shaft is unbalanced by two identical attached weights, which cause a counterclockwise centrifugal couple, the unbalance may be reduced or removed by attaching balancing weights that produce a clockwise centrifugal couple of similar or the same amplitude. A rotating system of mass is in dynamic balance when rotation of the system does not produce any resultant periodic variations in the centrifugal force or couple, or vibration. If a system is initially unbalanced, to avoid the stress upon the bearings caused by the centrifugal force or couple, counterbalancing weights can be added.

Under conditions where the rotating speed is very high, even if the system mass is low, balance of the rotating system may still need to be considered, for example, to avoid large vibrations and system or component failure.

In view of these concerns, in some embodiments and as illustrated in FIGS. 5, 7 and 13A-13D, motor 110 may include a coaxial balance weight 135 and a balance weight 137 integrated with the rotor 130, or connected to the rotor 130, for counteracting any unbalanced weight introduced by the motion conversion coupling member 150 (e.g. crank 152 and crank bearing 156), or present in the rotor 130 itself, to reduce possible dynamic unbalance, thus reducing potential vibrations in the motor 110.

Another possible approach to balance the weight of a rotation system is to remove certain mass from the system at selected counterbalancing locations. For example, cavities such as openings or holes may be provided in the rotor 130, which may be located and sized to provide static or dynamic balance, or both. A further benefit of this approach is that the overall weight of the rotating mass is reduced, which can additionally reduce vibration and the stress in the system.

For example, as can be better seen in FIG. 5, rotor body 136 may include openings 139, which are cavities shaped, sized, and located to provide static and dynamic balance. Specifically, openings 139 are located at the side of the rotor 130 where the crank 152 and crank bearing 156 are attached to the rotor 130, so that the weight/load added by crank 152 and crank bearing 156 are at least partially off-set (balanced) by the openings 139. As a result, possible unbalanced centrifugal and vibrations induced by crank 152 and crank bearing 156 can be reduced. Any remaining unbalance may be addressed by adding one or more balancing weights, but the balancing weights can now be smaller and lighter as compared to a rotor without the weight balancing openings 139.

Figure 13D:
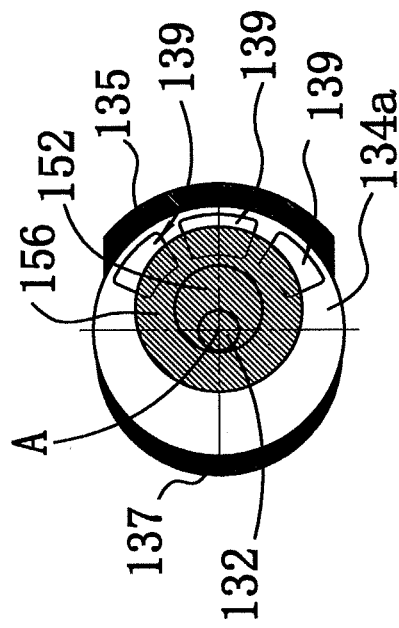
FIG. 13D is a simplified axial view of the rotor.
Figure 13C:
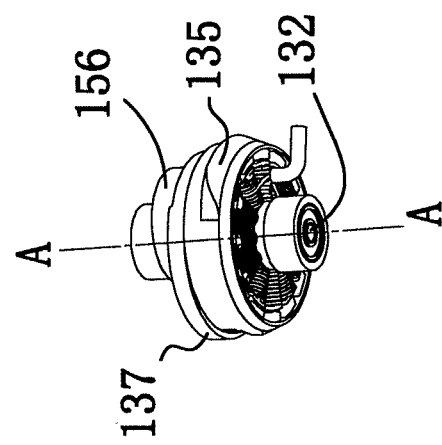
FIG. 13C is a perspective view of the rotor.

As can be better seen in FIGS. 5, 7, and 13A to 13D, balancing weights 135 and 137 may be positioned and distributed close to the perimeters of the rotor body. For example, balancing weights 135 and 137 are provided at the outer perimeter of rotor body 136 on the opposite sides. Conveniently, when the balancing weights are positioned further away from the rotation axis A, less mass may be used to provide the same balancing effect as compared to weights positioned closer to the rotation axis A. In particular, FIG. 13B shows schematically the centrifugal forces generated by rotation of the rotor 130. F1 represents the centrifugal force generated by crank 152 and crank bearing 156. F2 represents the centrifugal force generated by balancing weight 137, including the effects of the openings 139. F3 represents the centrifugal force generated by balancing weight 135. Balancing weight 135 is offset from the rotation axis A on the same side as the crank 152, and balancing weight 137 is offset from the rotation axis A on the opposite side. As a result, F1 and F3 are of the same direction, and opposite the direction of F2. Assuming the distance between the acting points of F1 and F2 along the axis A is X1, and the distance between F2 and F3 is X2, the distance between F1 and F3 is X1+X2. To achieve dynamic balance, for force balance, F1+F3=F2, and for couple balance, F1×X1=F3×X2. As can be appreciated, for achieving static balance only, F3 may be zero. As now can be appreciated, embodiments disclosed herein can provide smooth and efficient rotation to translation conversion in a tattoo device or machine, with improved static and dynamic balance, and reduced vibration and noise.

It can now be further appreciated that the embodiments illustrated in the drawings may be modified and still retain at least some of the benefits described herein.

For example, as shown in FIG. 3D, the slotted slider 154 may be coupled to the crank 152 directly without a crank bearing. The crank 152 may slide in the slot of the slotted slider 154 during operation and be in direct contact with the slotted slider 154.

Figure 12:
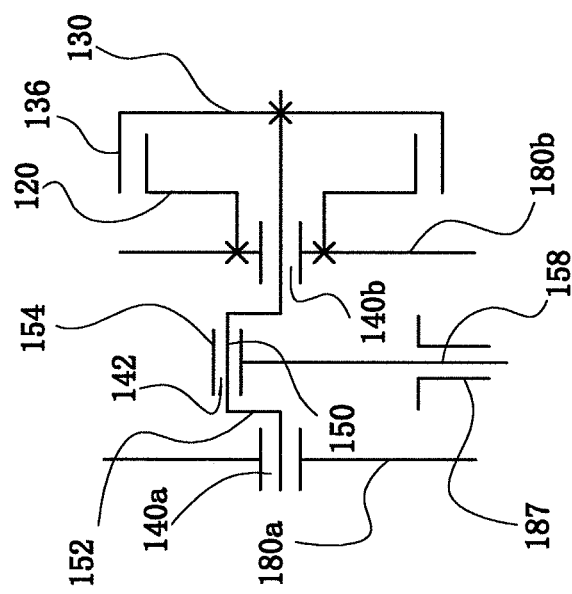
FIG. 12 is a schematic diagram illustrating a further possible arrangement of the components in a motor for use in the device of FIG. 1.

As another example, the rotor body 136 may be positioned between the bearings 140 for the motor arrangement in the embodiments illustrated in FIGS. 1-10. However, in some alternative embodiments, a portion of the rotor 130, such as the rotor body 136 of the rotor 130 may be positioned outside the bearings 140 that support the rotor shaft 132, as illustrated in FIG. 12. The windings of the stator 120 in this example are also positioned on the right side of the right bearing so the windings of the stator 120 are still aligned with the magnets on the rotor body 136, as can be seen in FIG. 12. The motion conversion coupling member 150 is still supported between the bearings 140.

While separate frames components, such as frames 180 and 190, are shown in the drawings and provided in some described embodiments, in other embodiments, the motor 110 may have a unitary frame 170 to which the motor components are mounted. The frame 170 may be included or integrated in the housing body 104. The bearings 140 may be mounted indirectly to any frame component or unitary frame or housing body, as long as the bearings 140 are secured in position relative to the motor housing and the stator 120. Further, the housing body or frame of the motor 110 may be combined and incorporated into the housing or frame for the entire base unit 100, which houses both the actuator 108 and the needle-driving shaft 158. In other words, the frame to which the bearings 140 are mounted to or mounted on may be a frame in the motor or a frame as a part of the actuator, or, may alternatively be a frame of the base unit. In some embodiments, the base unit 100 may have a separate frame or housing for mounting or housing the actuator 108 as well as the needle-drive shaft 158 and other components.

In some embodiments, the base unit 100 may have an open structure where the actuator 108 or motor 110 is exposed and not enclosed in any additional outer housing, other than a frame to which the motor components and the motion conversion coupling members are mounted. That is base unit 100 may have a frame supporting the bearings 140 where the frame does not form a complete enclosure enclosing the motor 110.

When a bearing 140 is mounted to a frame or a wall, the bearing may be mounted directly in or on the wall, such as at a surface of the wall, or in a recess or a bore in the wall. The bearing may also be mounted indirectly to the wall, such as through the stator or through another stationary component in the motor 110. The bearings may enclosed by the wall to reduce footprint. However, a bearing may be positioned beside the wall for any reason. If the bearings 140a and 140b are spaced further away from each other, more components may be supported in between.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:
1. A tattoo device comprising:
a frame; and
an actuator for actuating a needle-driving shaft, the actuator comprising an electric motor comprising
  a stator mounted to the frame,
  first and second bearings mounted to the frame, and
  a rotor comprising a rotor shaft rotatably supported at the first and second bearings, and
  a motion conversion member for converting rotation motion of the rotor to translation motion for reciprocally actuating the needle-driving shaft, the motion conversion member positioned between the first and second bearings.
2. The tattoo device of claim 1, wherein the actuator comprises the frame.
3. The tattoo device of claim 2, comprising a housing, wherein the actuator and the needle-driving shaft are housed in the housing.
4. The tattoo device of claim 1, wherein the frame comprises a wall having first and second opposite sides, the first bearing is mounted to the first side of the wall, and the second bearing is mounted to the second side of the wall.
5. The tattoo device of claim 1, wherein the first bearing is mounted directly on the frame, and the second bearing is mounted on the stator and indirectly to the frame.
6. The tattoo device of claim 5, wherein the stator comprises a bushing fixedly mounted at the second side of the wall, the bushing comprising a recess or bore, and the second bearing being mounted in the recess or bore.
7. The tattoo device of claim 1, wherein the motion conversion member comprises a crank and a slotted slider coupled to the crank.
8. The tattoo device of claim 7, wherein the slotted slider is coupled to the crank through a crank bearing.
9. The tattoo device of claim 1, wherein the motion conversion member comprises a cam.

10. The tattoo device of claim 1, wherein the motion conversion member comprises a slider-crank linkage or slider-crank mechanism.

11. The tattoo device of claim 1, wherein the motion conversion member is fixedly mounted on the rotor.

12. The tattoo device of claim 11, wherein the motion conversion member is fixedly mounted on the rotor shaft.

13. A tattoo device comprising:
 an actuator for actuating a needle-driving shaft, the actuator comprising
  an electric motor comprising
   a stator,
   first and second bearings, and
   a rotor comprising a rotor shaft rotatably supported at the first and second bearings, the rotor rotatable about a rotation axis of the rotor shaft, and
  a motion conversion member coupled to the rotor for converting rotation motion of the rotor to translation motion for reciprocally actuating the needle-driving shaft, the motion conversion member having an unbalanced weight with respect to the rotation axis,
 wherein the rotor comprises a balancing portion shaped and configured to at least partially offset the unbalanced weight of the motion conversion member so as to reduce vibration caused by the unbalanced weight of the motion conversion member during rotation of the rotor.

14. The tattoo device of claim 13, wherein the balancing portion of the rotor is shaped and configured to improve static balance.

15. The tattoo device of claim 14, wherein the balancing portion of the rotor is further shaped and configured to reduce dynamic unbalance caused by the unbalanced weight of the motion conversion member.

16. The tattoo device of claim 13, wherein the balancing portion of the rotor comprises a cavity on the rotor.

17. The tattoo device of claim 13, wherein the motion conversion member comprises a crank and a slotted slider coupled to the crank, and the unbalanced weight comprises a weight of the crank.

18. The tattoo device of claim 17, wherein the slotted slider is coupled to the crank through a crank bearing, and the unbalanced weight further comprises a weight of the crank bearing.

19. The tattoo device of claim 13, wherein the motion conversion member comprises a cam, and the unbalanced weight is a weight of the cam.

20. The tattoo device of claim 13, wherein the motion conversion member comprises a slider-crank linkage or slider-crank mechanism.

21. The tattoo device of claim 13, wherein the balancing portion of the rotor comprises an added weight.

22. The tattoo device of claim 13, wherein the electric motor is an outrunner brushless direct-current motor, and the rotor comprises a rotor body having a generally bell or cup shape.

23. The tattoo device of claim 13, comprising a housing, wherein the actuator and the needle-driving shaft are housed in the housing.

* * * * *